United States Patent [19]

Stevens et al.

[11] Patent Number: 5,247,966
[45] Date of Patent: Sep. 28, 1993

[54] SUCTION IRRIGATOR VALVE APPARATUS

[75] Inventors: Jon A. Stevens, South Lake Tahoe, Calif.; Roger R. Hill, Silver Springs, Nev.

[73] Assignee: Tahoe Surgical Instruments, Inc., Zephyr Cove, Nev.

[21] Appl. No.: 640,242

[22] Filed: Jan. 11, 1991

[51] Int. Cl.⁵ .......................................... F16K 11/065
[52] U.S. Cl. ........................... 137/625.69; 137/625.48; 251/900; 604/33; 604/249
[58] Field of Search ....................... 137/625.48, 625.69; 251/900; 604/33, 249

[56] References Cited

U.S. PATENT DOCUMENTS

| 2,633,324 | 3/1953 | Bierman | 137/625.48 |
| 2,912,007 | 11/1959 | Johnson | 137/625.64 X |
| 3,678,959 | 7/1972 | Liposky | 604/33 X |
| 3,722,800 | 3/1973 | Shames et al. | 137/625.48 X |
| 3,771,565 | 11/1973 | Padula | 137/625.64 |
| 3,870,045 | 3/1975 | Vaughan | 604/249 X |
| 3,951,166 | 4/1976 | Whitener | 137/625.69 X |
| 3,993,099 | 11/1976 | Nightingale | 137/625.48 |
| 4,502,508 | 3/1985 | Lester | 137/625.69 |
| 4,668,215 | 5/1987 | Allgood | 604/30 |
| 4,881,523 | 11/1989 | Heckele | 128/4 |

FOREIGN PATENT DOCUMENTS 2824720 12/1979 Fed. Rep. of Germany ........................ 137/625.69

OTHER PUBLICATIONS

Karl Storz Endoscopy Brochure.
Cabot Medical Brochure entitled "Introducing the Corson Disposable Suction/Irrigation Probe" Apr. 1990.
Apple Medical Corporation, Brochure entitled "Laparoscopic cholecystectomy".

Primary Examiner—Gerald A. Michalsky
Attorney, Agent, or Firm—Limbach & Limbach

[57] ABSTRACT

A device for irrigation and suction removal of blood, bodily fluids and debris from a body cavity primarily during laparoscopic procedures and surgery. The device contains a single piston slidably disposed in a passage contained in a housing having two inlets and a single outlet. The piston includes a central seal with two valve portions positioned on each side of the central seal. Piston positioning means are provided to move the piston to align the valve portions within the housing with the outlet and one of the inlets, while the other inlet is simultaneously sealed off. Thus, the piston may be moved from a neutral or shut-off position to an open irrigation position, or, alternately, moved from the neutral or shut-off position to an open vacuum position. The valve may also contain automatic biasing means for returning the valve from either the open-irrigation position or the open-vacuum position to the central shut-off position.

5 Claims, 3 Drawing Sheets

SUCTION IRRIGATOR VALVE APPARATUS

TECHNICAL FIELD OF THE INVENTION

This invention relates generally to an apparatus for the flushing of an internal body cavity and, alternately vacuuming excess fluid or body tissue primarily during surgery. The apparatus has the capability of providing a vacuum force to remove blood, tissue, and liquid from a body cavity and alternately providing an irrigation flow, such as a sterile cleansing solution, into the body cavity. An attachment for the access of a flexible instrument such as fiber optic bundle is also provided.

BACKGROUND OF THE INVENTION

It is necessary during certain surgical procedures, such as, but not limited to, laparoscopic or surgical procedures, to provide a source of irrigation fluid and, alternately, a suction or vacuum force to a body cavity. It is also common during the above described procedures to provide a flexible instrument such as a fiber optic bundle or endoscope into the body cavity. The procedure may be carried out with the use of instruments that may provide all three functions.

The use of presently available devices have certain drawbacks. For example, a device that provides a suction force and an irrigation stream to a body cavity utilizes two independent button activated valves which are independently operated. The described device has the undesirable drawback in that both valves can be inadvertently depressed creating flow of irrigation stream into the vacuum line thereby resulting in wasted time and energy in order to clean and flush the line.

Another drawback of the above described invention is the gradual buildup of blood and tissue in a common cavity joining the irrigation and vacuum passages. The result is that the blood and tissue are eventually mixed into the irrigation stream and carried back into the body cavity. The specific drawback is the potential of contamination of the irrigation solution and the waste of valuable time and irrigation solution in having to further suction out the blood and tissue that was flushed back into the body cavity.

Another example of a device presently available is the invention described in U.S. Pat. No. 4,881,523, which utilizes a single valve and a single plunger in providing an irrigation stream and a suction force. But, as with the above described invention, the device has the drawback of an intermediate position which allows a common passage between the irrigation flow and the suction passage, thus, having the same critical problems as the above described device.

It is thus an object of the present invention to provide a simple device to enable the practitioner to provide a suction force, and, alternately an irrigation stream to a body cavity.

It is yet a further object of the present invention to provide a device which does not provide a common passage between the irrigation stream and a suction passage.

It is still yet another object of the present invention to provide the practitioner with a device that provides an irrigation stream and a suction force which is operated conveniently by the use of a single hand.

It is still further yet another object of the present invention to allow for the access of the flexible instrument through such a device without interfering with the functions thereof.

SUMMARY OF THE INVENTION

In order to achieve these objects, the present invention is directed to a device for tissue irrigation during surgical procedures and, alternately, the vacuum or suction removal of blood, tissue and fluids from a body cavity during such procedures. The device comprises a body or housing which contains a generally longitudinal passage or cavity (defining a longitudinal axis) extending through the body or housing.

A first irrigation inlet opening, a second vacuum inlet opening and a third vacuum and irrigation outlet opening extend from the exterior of the housing into the interior passage. The third opening is located between the first and second openings along the longitudinal axis of the cavity within the housing.

A piston is disposed within the interior cavity of the housing and along the longitudinal axis thereof. The piston is shaped such that, in use, a central seal or sealing surface formed thereon may be located between the first and second openings in the housing, and such that the third opening (the outlet) is blocked or shut off from communication from the first and second openings. In such a central sealing position all openings are sealed off from one another. The piston is further shaped to define two valve portions on either side of the central seal. Piston positioning means are provided to move the piston to align the valve portions within the housing with the outlet and one or the other of the vacuum or irrigation inlets, while the other inlet is sealed off.

The invention may utilize a biasing means for forcing the piston from an open irrigation position or an open vacuum position to the central seal or neutral position.

BRIEF DESCRIPTION OF THE DRAWINGS

The invention will be further understood by reference to the appended drawing figures in which.

DETAILED DESCRIPTION OF THE INVENTION

The present invention will be described with reference to the preferred embodiment shown in the figures.

Figure 1:
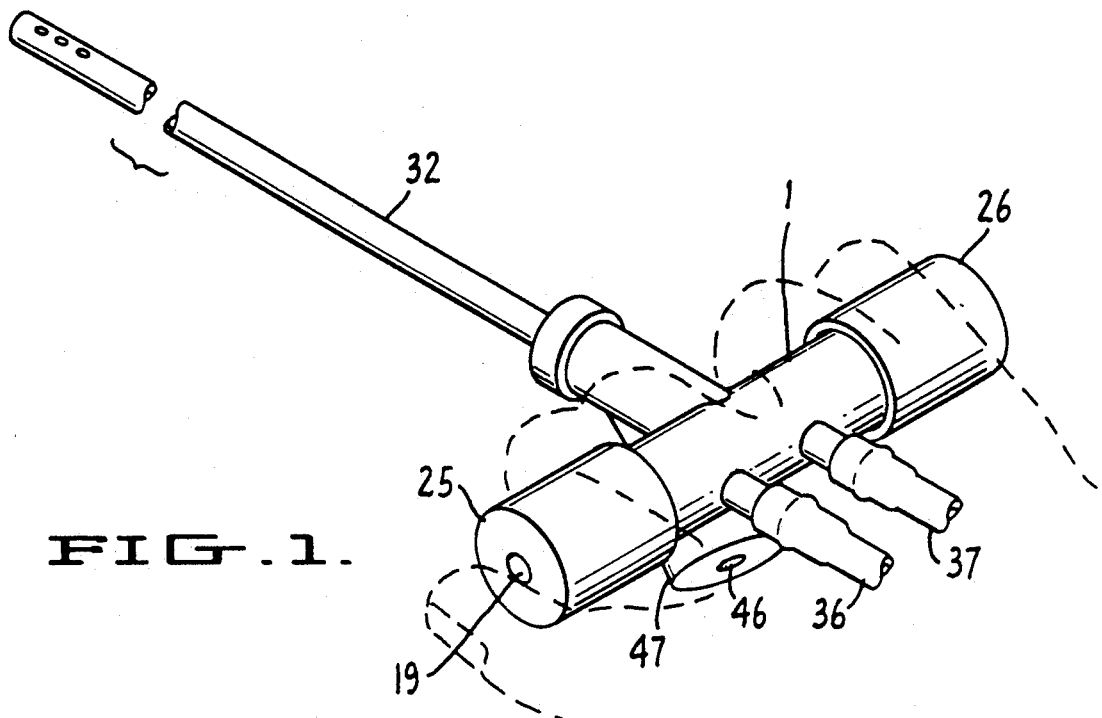
FIG. 1 is a external view of the preferred embodiment of the present invention held within a practitioner's hand.

FIG. 1 shows the device of the invention held within a human hand during operation. Generally, each of FIGS. 1-4 show a valve housing 1, which housing may be formed from any suitable inert material such as stainless steel. In the preferred form of the invention body 1 is formed of a plastic material such as polyphthalate carbonate (such as Lexan PPC) and is therefore inexpensively manufactured and disposable. It will be appreciated that many parts of the invention can be formed from such materials, i.e. stainless steel or plastic, or other materials, the choice depending on the cost of manufacture and the intended market. If the product is intended to be reusable the material must be sufficiently stable to be routinely subjected to sterilizing conditions, for example in an autoclave. On the other hand, disposable products need only meet the requirement that they be stable and inert with respect to the conditions under which they will be used.

Figure 2:
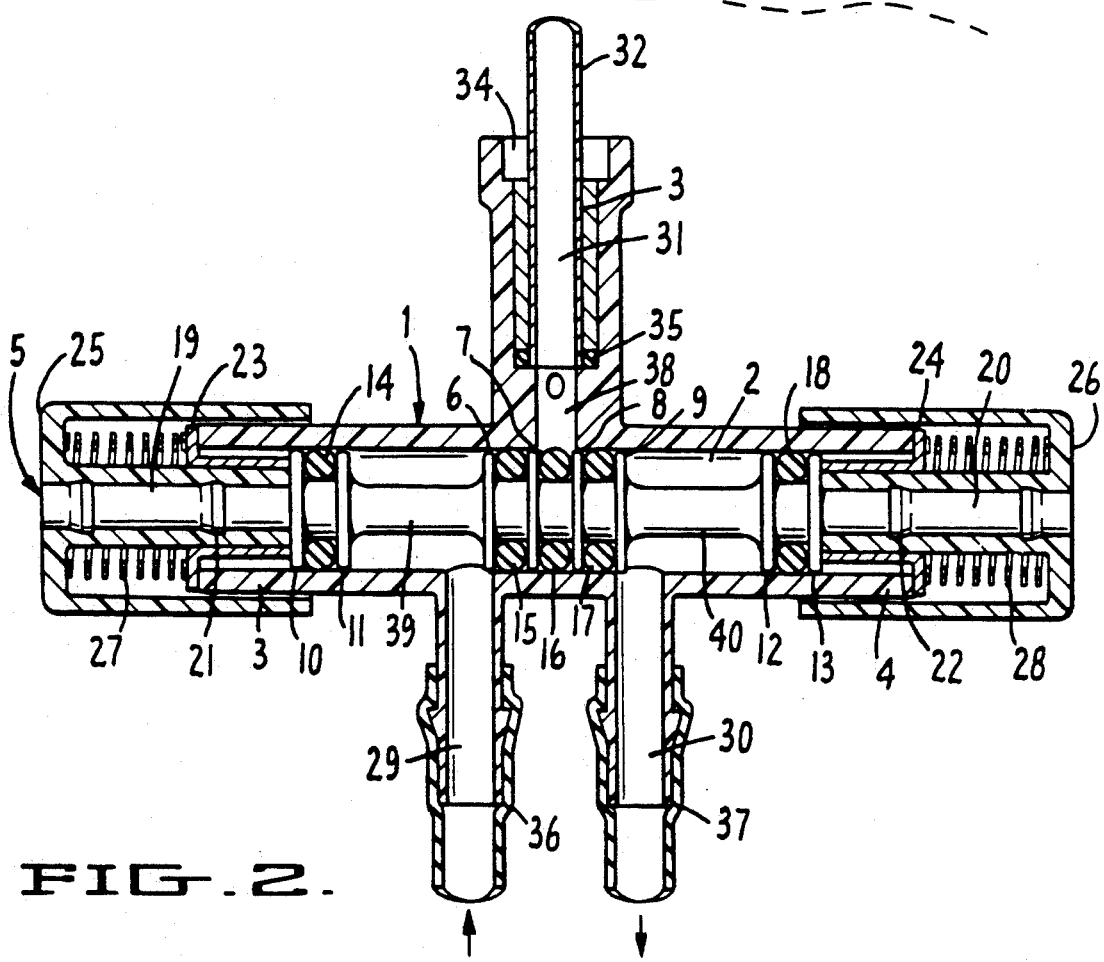
FIG. 2 is a cross sectional top view of the valve housing wherein the piston is shown in a central sealed position.
Figure 3:
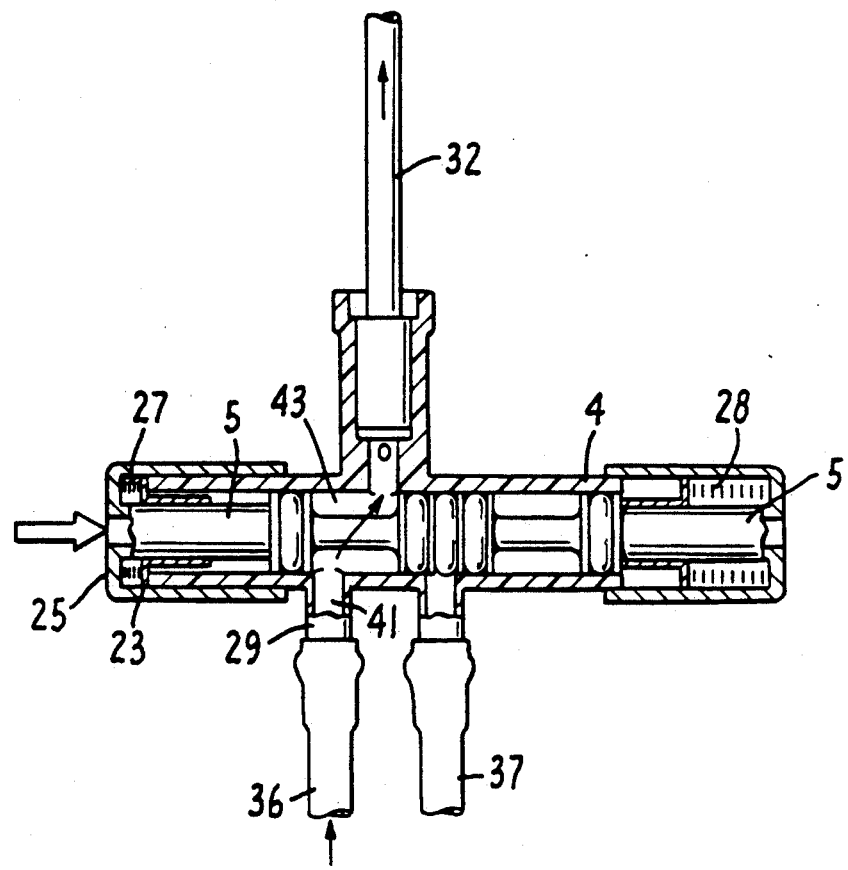
FIG. 3 is a cross sectional view of the present invention wherein the piston is shown in an open irrigation position.
Figure 4:
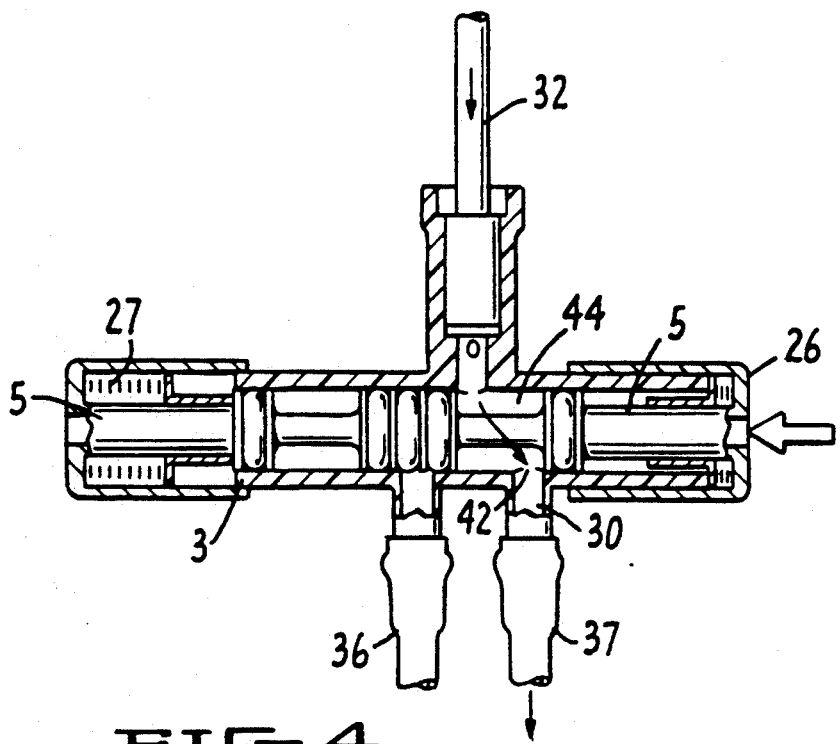
FIG. 4 is a cross sectional view of the present invention wherein the piston is shown in an open vacuum position.

FIGS. 2-4 show valve housing 1 having a cylindrical cavity 2 extending longitudinally through the housing from a first end 3 to the second end 4. A piston 5 is positioned within the passage 2. Like body 1, piston 5 may be constructed of a metal or plastic, and in the preferred case will be polyphthalate carbonate, i.e. Lexan PPC. Piston 5 is configured with four circular flanges 6-9 located at the center of the piston. Piston 5 is further configured with four additional flanges 10-13, i.e. two each located at each end of the piston 5. "O" rings 14-18 are placed between the flanges in use. "O" rings 14-18 are made from any suitable material which will provide a satisfactory seal along the inner surface of cavity 2.

In the preferred embodiment actuating buttons 25 and 26 are positioned on the end most portions of piston 5, separately numbered 19 and 20 in FIG. 2. Locking interfaces 21 and 22 are formed on end most portions 19 and 20 respectively such that buttons 25 and 26 can snap fit on either end of the piston. Flanged sleeve stops 23 and 24, constructed of either plastic or stainless steel, as well as compression springs 27 and 28 are positioned before buttons 25 and 26 are snapped into position. In the preferred embodiment springs 27 and 28 are double action equalizing springs of stainless steel, which may be obtained for example from the Smalley company of Ill. Such springs provide for an especially smooth feel when buttons 25 and 26 are pressed in use, and therefore provide a better tool for the practitioner. Springs 27 and 28 are respectively set against the flanged sleeve stops 23 and 24. Those skilled in the art will appreciate that other means for biasing the piston in the manner obtained by using springs 27 and 28 could be used, again depending on the requirements for a given application, i.e. disposable or reusable.

FIGS. 2-4 show inlet tubes 29 and 30 located at openings on one side of the housing 1. Tube 31 is located at an opening on the opposite side of the housing, the opening being longitudinally located between the opening for tubes 29 and 30. Naturally these openings could be positioned in a number of orientations other than that shown in this preferred embodiment, limited only by the need to ensure that there are at least two inlet ports and one outlet port, and that the configuration of the openings allows for alternative communication between either of the tubes acting as an inlet with the tube acting as an outlet. The arrangement must not allow direct communication between the two inlet ports regardless of the piston position within the communication passage.

Probe 32 is shown inserted into tube 31. In the preferred embodiment probe 32 is held in place by an epoxy seal, indicated at 34. Alternatively, an internal push-in snap ring may be used. An "O" ring seal 35 is shown where the base of probe 32 rests against housing 1. Supply tubing 36 is shown placed over hollow tube 29 and is configured to be attached to an irrigation line. Supply tubing 37 is shown placed over hollow tube 30 and is configured to be attached to a vacuum line.

FIG. 1 shows the preferred embodiment of the invention in a neutral or central shut-off position. Piston 5 is in a "rest" position, situated so that the central flanges 6-9 and the "O" rings held therein seal-off outlet hole 38 from communication with cavity 2. Valve portions 39 and 40 are formed on the piston on each side of the central seal formed by flanges 6-9. Outer seals are formed by flanges 10-13 and "O" rings 14 and 18.

FIG. 3 shows the preferred embodiment of the invention in the open-irrigation position. The practitioner, when desiring an irrigation flow, depresses button 25 (arrow) transmitting longitudinal motion to piston 5 in the direction of the second end 4, thereby compressing spring 27. Valve portion 39 (FIG. 2) moves in the direction of the second end 4 until it allows irrigation fluid to flow from tube 29 into probe 32. When the practitioner releases button 25, the stored energy in the compressed spring 27 forces piston 5 back towards first end 3. The piston's motion is interrupted upon contact with flange sleeve 23 or flange sleeve 24 or both to reach the intermediate shut-off position illustrated in FIG. 2.

FIG. 4 shows the preferred embodiment of the invention in the open-vacuum position. During use the practitioner may alternately desire a suction force. To achieve this, the practitioner would depress button 26 (arrow), transmitting longitudinal motion to piston 5 in the direction of first end 3, compressing spring 28. Valve portion 40 (FIG. 2) moves in the direction of the first end 3 until it allows a suction force to flow through probe 32. When the practitioner releases button 26, the stored energy in compressed spring 28 forces piston 5 back towards second end 4. The piston's motion is interrupted upon contact with flange sleeve 24 or flange sleeve 23 or both to reach the intermediate shut-off position as illustrated in FIG. 2.

Figure 5:
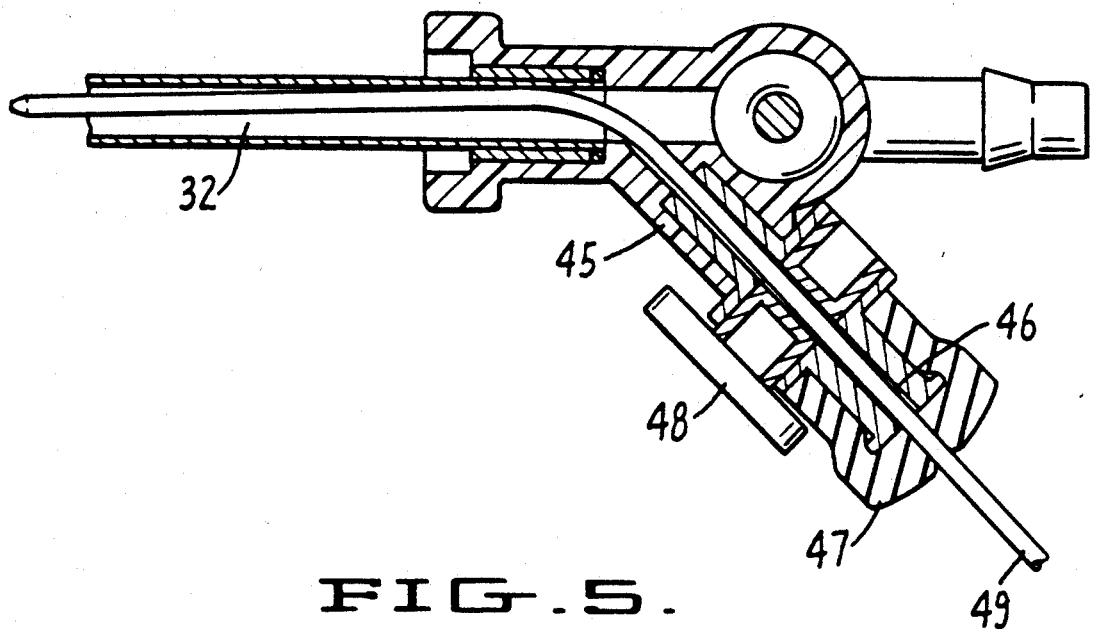
FIG. 5 is an external side cross sectional view of the present invention wherein an integral side port attachment is shown.

FIG. 5 shows an additional preferred embodiment of the invention which includes a side port configured to allow access of a flexible instrument through the valve body without interrupting the function of the suction irrigation device. In this embodiment the valve body housing is shaped to form a side port 45 containing a narrow passage 46. A rubber dam seal 47 is placed over the outerpost portion of passage 46. A flexible instrument such as a fiber optic bundle 49 is inserted through seal 47, continuing through the side port 45 and into hollow tube 31, finally extending into the hollow probe 32. A standard one-way medical on-off valve stopcock 48 available from the Malenkrodt company, is shown permanently bonded to the side port 45, using an acrylic adhesive or solvent bonding technology. Valve 48 is turned off to prevent fluids from flowing through the narrow passage 46 when side port 45 is not being used to hold a flexible instrument.

In use the suction irrigation device of the present invention affords the practitioner substantial advantages over those devices of prior art. The invention allows for the practitioner to operate the suction irrigation device with one hand. When not in use the device is designed to automatically return to a central fully sealed position. No by-pass of irrigation solution directly to the vacuum line is possible.

While the preferred embodiment shown in the figures is depicted as having particular shapes for its external and internal surfaces, skilled artisans will apreciate that other functional and cosmetic changes are possible without departing from the true spirit of the invention. For example, the shapes and/or colors of buttons 25 and 26 might be varied to provide the practitioner with improved grip, or to color code the vacuum and irrigation functions. Naturally, the single piston could also be positioned from one side, by pushing and pulling the piston from that side rather than utilizing the to and fro action of the preferred embodiment. While the spring loaded self centering feature of the invention is considered advantageous, it would also be possible to utilize such to and fro action, but have the piston rest in any of the three desired postions, i.e. vacuum open/irrigation closed, fully closed, or irrigation open/vacuum closed. We believe, however, that the embodiment shown in the figures provides the greatest ease of use.

What is claimed is:

1. An apparatus for alternatively allowing passage of an irrigating fluid and the application of a vacuum therethrough comprising:
   (1) a body having an internal cavity defining a longitudinal axis;
   (2) a vacuum inlet opening passing from the exterior of said body to said cavity;
   (3) an irrigation inlet opening passing from the exterior of said body to said cavity;
   (4) a vacuum and irrigation outlet opening passing from the exterior of said body to said cavity, said outlet being positioned along said longitudinal axis between said vacuum inlet opening and said irrigation inlet opening; and
   (5) a piston disposed within said cavity and along said longitudinal axis, said piston comprising:
      (a) a first, a second, a third, and a fourth sealing portion disposed along said longitudinal axis, each sealing portion including an O-ring,
      (b) a first waisted portion disposed between said first sealing portion and said second sealing portion,
      (c) a second waisted portion disposed between said third sealing portion and said fourth sealing portion,
      (d) a central sealing portion disposed between said second sealing portion and said third sealing portion, said central sealing portion substantially filling said cavity over a portion of said longitudinal axis,
   said piston being slidable along said longitudinal axis from a central off position, wherein said central sealing portion and said second and third sealing portions together seal said vacuum and irrigation outlet opening, to one of an irrigate position and a vacuum position,
   said first, second, third, and fourth sealing portions, said first and second waisted portions and said central sealing portion being disposed along said longitudinal axis relative to said irrigation inlet opening, said vacuum inlet opening, and said irrigation and vacuum outlet opening such that:
      said first waisted portion and said first and second sealing portions together provide a sealed passage between said irrigation inlet opening and said irrigation and vacuum outlet opening only when said piston is slid to said irrigate position, and seal said irrigation inlet opening when said piston is in said off position,
      said second waisted portion and said third and fourth sealing portions together provide a sealed passage between said vacuum inlet opening and said irrigation and vacuum outlet opening only when said piston is slid to said vacuum position, and seal said vacuum inlet opening when said piston is in said off position, and
      said central sealing portion together with said second and third sealing portions together:
         seal said vacuum inlet opening when said piston is slid to said irrigate position, and
         seal said irrigation inlet opening when said piston is slid to said vacuum position, and
   (6) a biassing means for biassing said piston to said off position.

2. The apparatus of claim 1 further comprising a longitudinal positioning means for longitudinally positioning said piston within said cavity in each of said irrigating, vacuum and off positions.

3. The apparatus of claim 2 wherein said piston comprises a rod having first and second ends and said longitudinal positioning means comprises first and second buttons positioned at said first and second ends of said rod and adapted for manual actuation.

4. The apparatus of claim 3, wherein the biassing means comprises a pair of compression springs positioned adjacent to each of the actuating buttons.

5. The apparatus of claim 1 further comprising a side port hole integral with said body, said side port being configured for a access of a flexible instrument without interference in the movement of said piston.

* * * * *